United States Patent
Howard et al.

(10) Patent No.: US 6,190,335 B1
(45) Date of Patent: Feb. 20, 2001

(54) OROFACIAL MYOGRAPHIC MEASUREMENT PROBE

(75) Inventors: Albert Howard, Sunnyvale; Ronald E. Tura, Alamo, both of CA (US)

(73) Assignee: Oro-Myographic Measuring Instrument, Inc., Concord, CA (US)

( * ) Notice: Under 35 U.S.C. 154(b), the term of this patent shall be extended for 0 days.

(21) Appl. No.: 09/480,810

(22) Filed: Jan. 10, 2000

(51) Int. Cl.$^7$ .................................................. A61B 5/103
(52) U.S. Cl. ........................ 600/590; 600/587; 73/379.02
(58) Field of Search ................................... 600/587, 589, 600/590, 595; 73/379.01, 379.02, 379.03, 379.09; 433/68, 71, 229

(56) References Cited

U.S. PATENT DOCUMENTS

| | | | |
|---|---|---|---|
| 2,708,367 | * 5/1955 | Lusk ........................................ | 73/379 |
| 4,488,873 | * 12/1984 | Bloomfield et al. .................... | 433/71 |
| 4,976,618 | * 12/1990 | Anderson .............................. | 433/215 |
| 5,090,421 | * 2/1992 | Wagoner, III ......................... | 128/774 |
| 5,190,051 | * 3/1993 | Wilson ................................. | 600/590 |
| 5,381,799 | * 1/1995 | Hamilton et al. ..................... | 600/590 |
| 5,452,727 | 9/1995 | Tura et al. ............................ | 128/777 |
| 5,609,161 | 3/1997 | Tura et al. ............................ | 128/777 |
| 5,954,673 | 9/1999 | Stachlin et al. ....................... | 600/590 |
| 6,050,961 | * 4/2000 | Arnold ................................. | 600/590 |

FOREIGN PATENT DOCUMENTS

93/18709 * 9/1993 (WO) .................................. 600/590

* cited by examiner

*Primary Examiner*—Cary O'Connor
*Assistant Examiner*—Charles Marmor, II
(74) *Attorney, Agent, or Firm*—Elliot B. Aronson

(57) ABSTRACT

An orofacial measurement probe for measuring muscle forces within the oral cavity. The probe includes a bite member sized for insertion into the oral cavity and a pressure-sensitive transducer disposed in transducer housing. The bite member is formed with a rigid upper portion, a rigid lower portion and an elastomeric member holding the upper and power portions in spaced-apart relationship to one another. The upper and lower portions are formed and arranged so that together with the elastomeric member they define a hydraulic cavity, which carries a hydraulic fluid. At least one of the upper and lower portions is formed to provide a bite surface sized for engagement by one or more of the patient's teeth. The transducer housing is separate from the bite member and arranged to be external to the oral cavity when the bite member is inserted into the oral cavity. The pressure-sensitive transducer disposed within the transducer housing is responsive to pressures sufficiently great that it can respond to the maximum bite force of a strong adult. The probe includes a connecting member connecting the hydraulic cavity with the transducer housing for maintaining the hydraulic cavity in hydraulic communication with the transducer. A patient biting down on the bite surface imparts a bite force to the hydraulic fluid in the hydraulic cavity that is transmitted to the transducer whereupon the transducer provides an electrical signal indicative of the bite force.

4 Claims, 3 Drawing Sheets

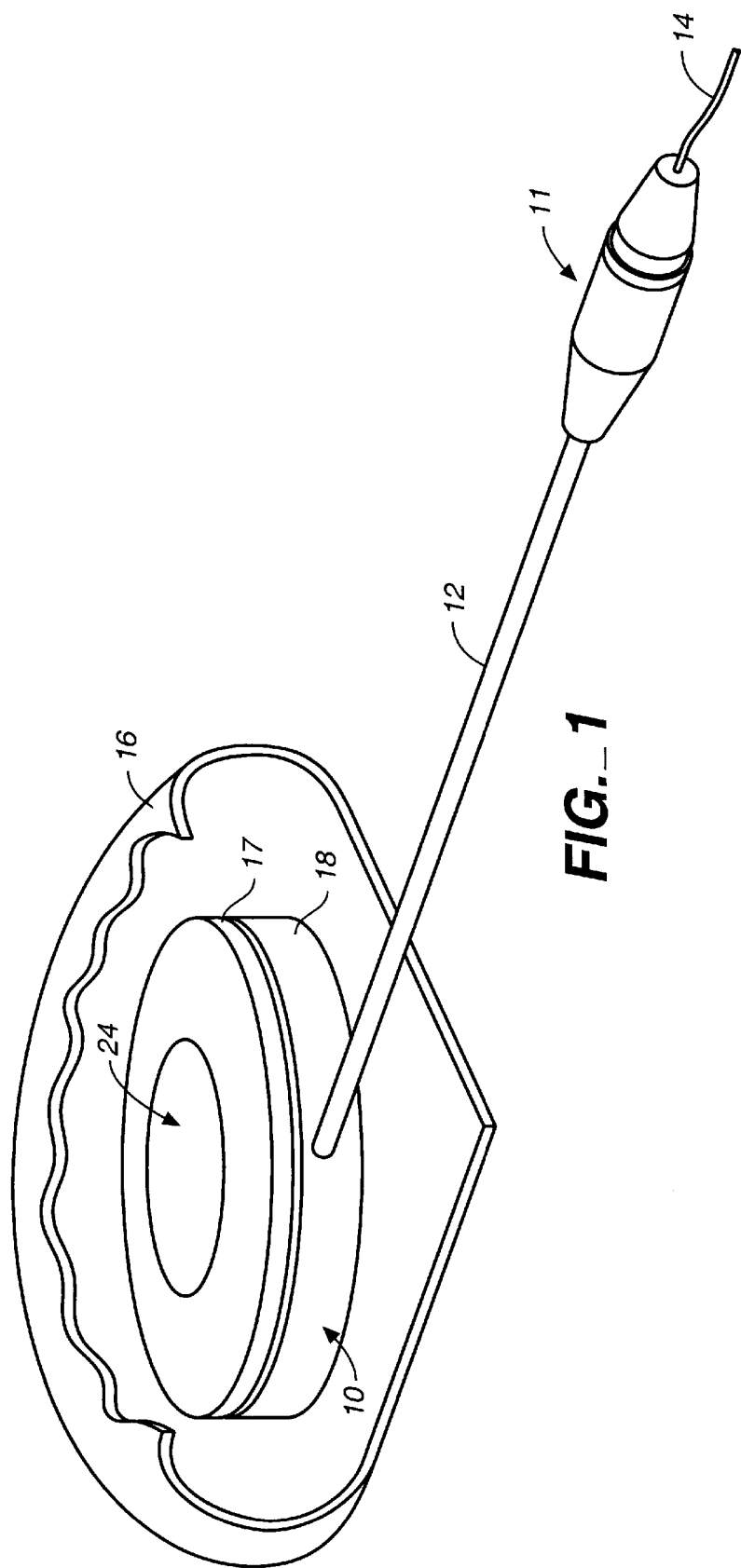
FIG._1

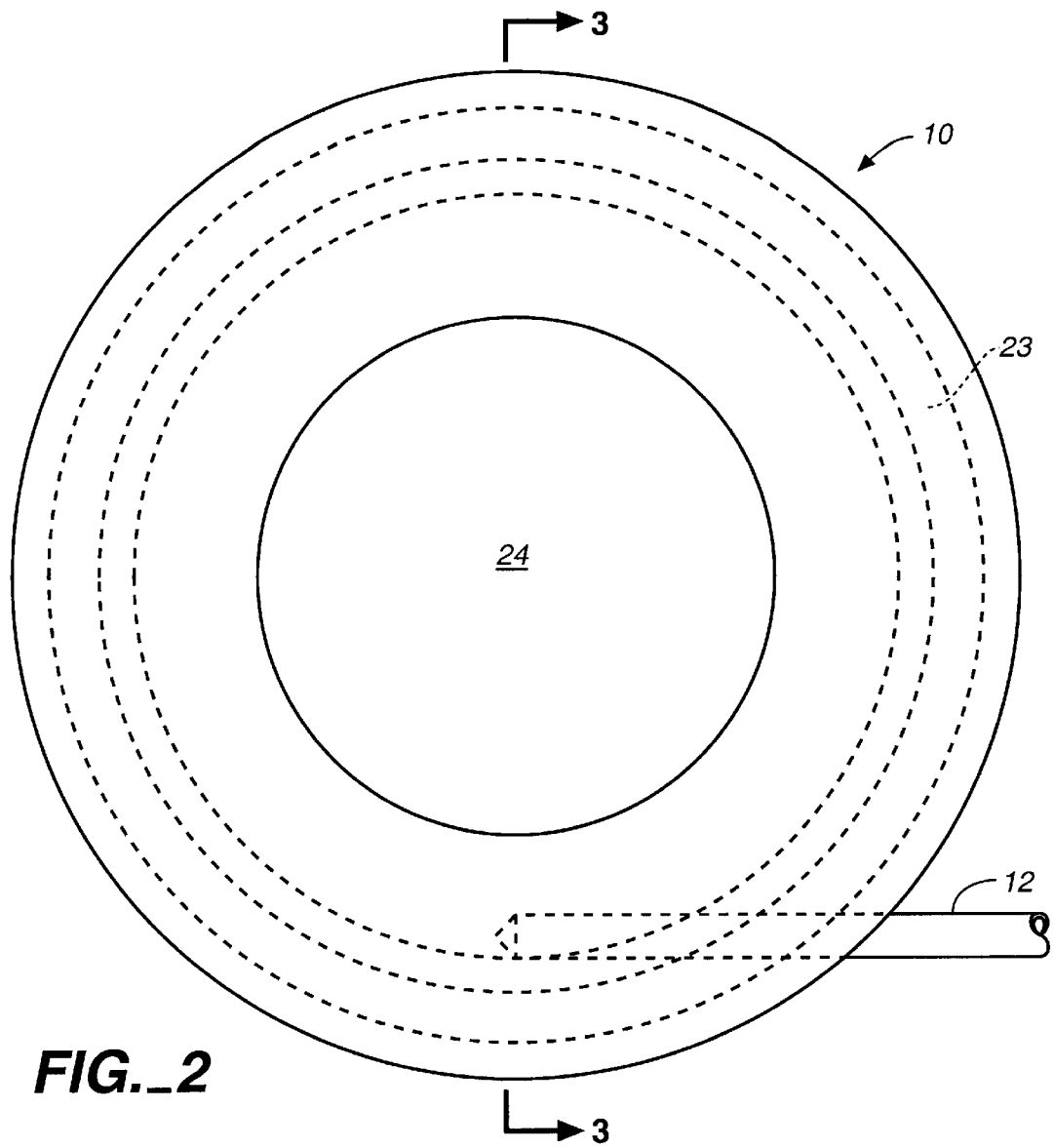
FIG._2
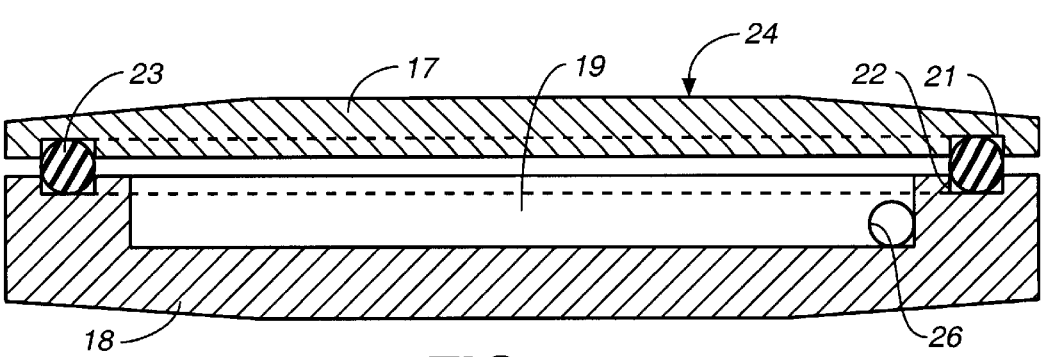
FIG._3

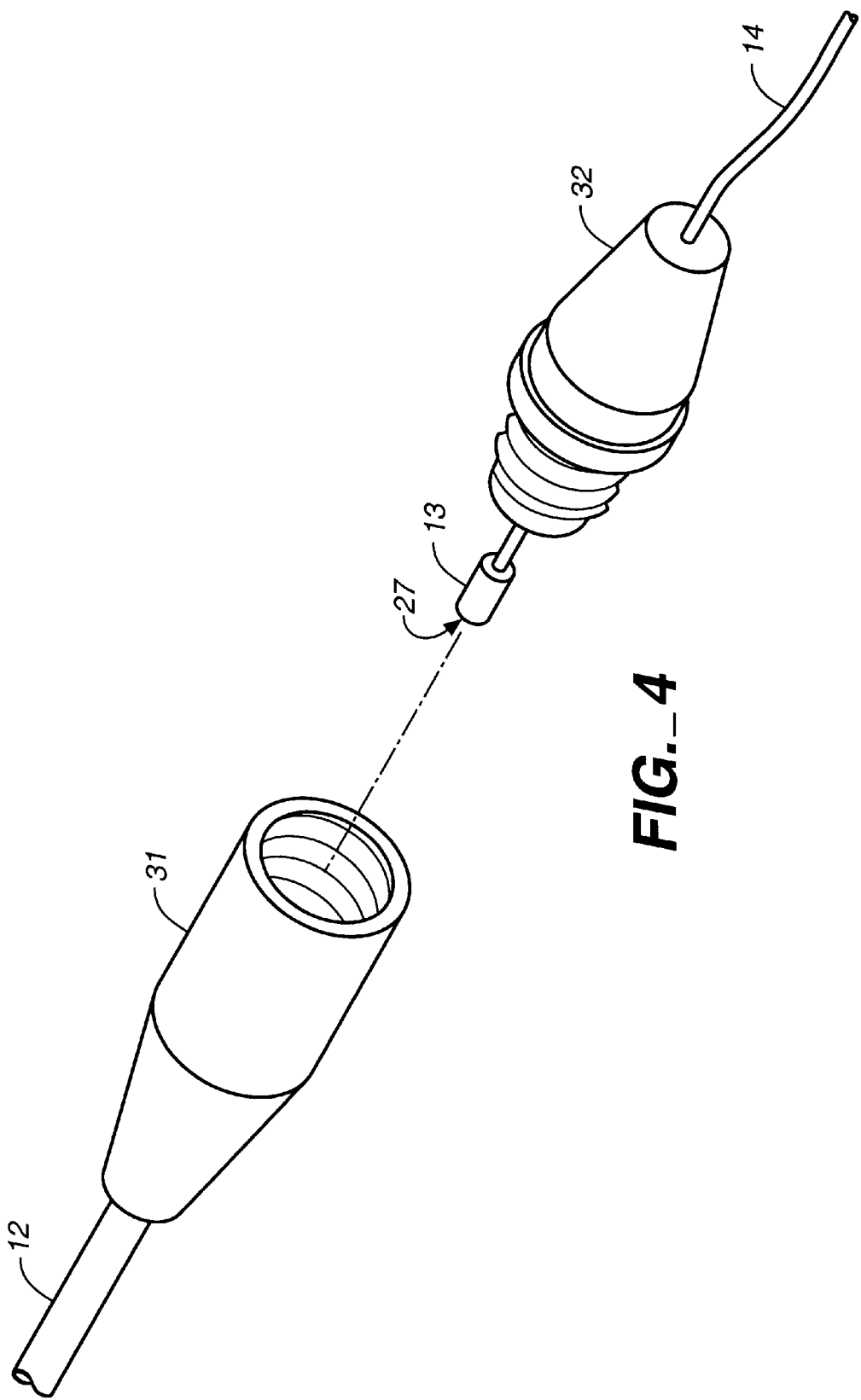
FIG._4

OROFACIAL MYOGRAPHIC MEASUREMENT PROBE

BACKGROUND OF THE INVENTION

The invention relates to probes for myographic measurements within the oral cavity.

Myography is concerned with the measurement of contractions and relaxations of the skeletal muscles. In the diagnosis and treatment of various disorders involving the face and mouth, it is often desirable to determine the strength of the face and mouth muscles. Such determinations may be useful, for example, in assessing and treating certain speech disorders, in assessing the need for physical therapy for stroke victims, to detect orofacial muscle imbalance, and for tracking progress in recovery from strokes or other injury to the mouth or face. Measurement of orofacial muscle strength may also be useful in connection with oral surgery, particularly where the musculature is to be cut. Measurements prior and post operation, for example, can aid in determining an appropriate course of isometric exercise or other physical therapy.

A system for direct measurement of orofacial muscle strength is disclosed in U.S. Pat. Nos. 5,452,727 and 5,609,161. Those patents provide an improved measurement technique especially suited to measurements in and about the oral cavity, and especially to measurements of lip and tongue muscle strength. As disclosed in those patents, the patient presses against a pressure-sensitive probe with the lips or tongue while the probe is held in a prescribed disposition typically with the aid of an ancillary support fixture. The probe generates an electrical signal characteristic of the applied force and hence the muscle strength.

The embodiment of probe disclosed in the above-referenced patents is illustrated in those patents for measurement of lip and tongue muscle strengths and is less suited for measurement of stronger muscle strengths, such as direct measurement of the strength of a patient's bite force.

SUMMARY OF THE INVENTION

The present invention provides an orofacial measurement probe extending the capabilities of the probes disclosed in the above-referenced U.S. patents. The present probe is able to measure strong muscle forces within the oral cavity without sacrificing convenience of use. In particular, the present probe is especially suited to measuring the force exerted by the masseter muscles when the patient bites down with maximum strength.

Briefly, a probe in accordance with the invention includes a bite member sized for insertion into the oral cavity and a pressure-sensitive transducer disposed in transducer housing. The bite member is formed with a rigid upper portion, a rigid lower portion and an elastomeric member holding the upper and power portions in spaced-apart relationship to one another. The upper and lower portions are formed and arranged so that together with the elastomeric member they define a hydraulic cavity, which carries a hydraulic fluid. In addition, at least one of the upper and lower portions is formed to provide a bite surface sized for engagement by one or more of the patient's teeth. The transducer housing is separate from the bite member and arranged to be external to the oral cavity when the bite member is inserted into the oral cavity. The pressure-sensitive transducer disposed within the transducer housing is responsive to pressures sufficiently great that it can respond to the maximum bite force of a strong adult. The probe includes a connecting member connecting the hydraulic cavity with the transducer housing for maintaining the hydraulic cavity in hydraulic communication with the transducer. A patient biting down on the bite surface imparts a bite force to the hydraulic fluid in the hydraulic cavity that is transmitted to the transducer whereupon the transducer provides an electrical signal indicative of the bite force.

Other aspects, advantages, and novel features of the invention are described below or will be readily apparent to those skilled in the art from the following specifications and drawings of illustrative embodiments.

BRIEF DESCRIPTION OF THE DRAWINGS

FIG. 1 is an overall view of an orofacial measurement probe embodying the invention.

FIG. 2 is a plan view of the bite member of FIG. 1.

FIG. 3 is a cross-sectional view of the bite member along the line 3—3 of FIG. 2.

FIG. 4 is an exploded view of the transducer housing and transducer of FIG. 1.

DETAILED DESCRIPTION OF ILLUSTRATIVE EMBODIMENTS

FIG. 1 shows an orofacial measurement probe including a bite member 10 for insertion into a patient's mouth, a transducer housing 11 and a connecting member 12. The transducer housing includes a pressure-sensitive transducer 13 (visible in FIG. 4) which responds to pressure applied to a pressure-sensitive surface and provides an electrical signal representative of the applied pressure. Transducer 13 is connected to an electrical cable 14 for carrying electrical signals representative of the applied pressure and, hence, of muscle strengths. In FIG. 1 bite member 10 is shown covered by a replaceable sterile protective sleeve 16 (partially cut away in FIG. 1).

Bite member 10 is formed of an upper portion 17 and an opposed lower portion 18, disposed so as to permit the upper and lower portions to be engaged by opposed upper and lower teeth. Upper and lower portions 17 and 18 are shaped and disposed to form a hydraulic cavity 19 (visible in FIG. 3). Matching annular grooves 21 and 22 are formed in the inner surfaces of upper and lower portions 17 and 18, respectively, for receiving an elastomeric member, which in the illustrated embodiment is provided by an o-ring 23. Lower portion 18 has been hollowed out to give volume to hydraulic cavity 19. The upper and lower portions are secured together by adhering each to o-ring 23 with a suitable adhesive. In the illustrated embodiment the upper and lwer portions of bite member 10 are formed of stainless steel. Oring 23 must be made of a material that can be fixed with adhesive to stainless steel. Moreover, to assure accuracy of measurement throughout the life of the probe, the adhesive should be resistant to the hydraulic fluid in cavity 19. That is, the adhesive should be such as not to deteriorate under contact with the hydraulic fluid. Deterioration of the adhesive may lead to microscopic leaks of hydraulic fluid, which will compromise measurement accuracy. If a deteriorated adhesive still retains its adhering power and at the same time permits microscopic leaks to develop, then the probe will falsely appear to be in working order leading to false results. In the illustrated embodiment o-ring 23 is formed of an acrylonitrile-butadiene copolymer generally referred to as Buna N, although other elastomeric materials may be used. The adhesive was a commercially available cyanoacrylate adhesive of the type commonly available under the name Krazy Glue.® Although these materials are disclosed here for purposes of illustration, those skilled in the art will appreciate that other materials meeting the purposes of the invention may be substituted and no limitation to these particular materials is intended.

O-ring 23 serves two functions. First, it provides a seal between the upper and lower portions to prevent hydraulic fluid from leaking out of hydraulic cavity 19. Second, it allows sufficiently small relative movement between the upper and lower portions that a bite force exerted by a patient may be transmitted through the rigid upper and lower portions to the hydraulic fluid in cavity 19. In effect, in the disclosed embodiment the upper and lower portions act like a pair of opposed pistons exerting force on the hydraulic fluid between them. O-ring 23 holds the upper and lower portions in spaced-apart relationship to one another to assure they will not meet under the action of a patient biting down on them. While the embodiment disclosed in the figures is particularly simple and effective, those skilled in the art given the benefit of this disclosure will nevertheless be able to design other configurations for imparting the bite force to the hydraulic fluid effective for the range of pressures arising in masseter muscle measurements in the oral cavity. Therefore, no limitation to the illustrated embodiment is intended.

In the illustrated embodiment bite member 10 is formed with a diameter of one inch so as to fit conveniently within the oral cavity. The central region of upper bite portion 17 is raised somewhat to define a centrally disposed bite surface 24 for engagement by one or more of the patient's teeth. In the illustrated embodiment bite surface 24 has a diameter of one-half inch and is raised 0.025 inch above the upper outside edge of upper portion 17. The raised bite surface serves to position the patient's bite squarely above and below the central portion of the bite member and thereby to discourage the patient from biting down on the edge of the bite member over o-ring 23, which could lead to a false reading. With a central, raised bite surface the patient's bite force is applied uniformly to the hydraulic fluid. In the illustrated embodiment only upper portion 17 is formed with a raised bite surface; however, lower portion 18 may also be formed with such a surface. The specific shape and size of bite surface shown here have been found to be convenient. Those skilled in the art will recognize that other sizes and shapes may also be used. Indeed, the bite member may be formed with an entirely flat upper surface and the bite member will nevertheless function for its intended purpose, provided only that care is exercised to assure that the patient does not bite down over the o-ring. Therefore, the invention is not intended to be limited only to the illustrated bite surface.

Connecting member 12 is provided in the illustrated embodiment by a thin stainless steel tube having an outer diameter of 0.125 inch and an inner diameter of 0.095 inch. Lower portion 18 of the bite member includes a bore 26 for receiving one end of connecting member 12, which may be welded in place for a rigid leak-proof connection. Structurally, connecting member 12 connects bite member 10 with transducer housing 11. Functionally it maintains hydraulic communication between hydraulic cavity 19 and the pressure-sensitive surface of transducer 13.

Connecting member 12 may also serve as a handle for manipulating the bite member in the oral cavity. In the illustrated embodiment connecting member 12 is one solid piece having a length of 3.625 inch. This size has been found convenient for use although other lengths may also be used. Those skilled in the art given the benefit of this disclosure will appreciate that other arrangements and configurations of connecting member may also serve the purposes of the invention. By way of example, the connecting member need not be rigid along its entire length, but may include a section of flexible tubing.

It is significant that transducer housing 11 is separated from bite member 10 by connecting member 12. In general it is difficult to get a suitable measurement gauge with covering sanitary sleeve that will fit in the oral cavity for making accurate measurements. Here the bite member is made smaller, lighter and more manipulable because it does not include the transducer that generates the representative electrical signal. The applied force of the patient's bite is then brought out of the oral cavity through connecting member 12 and applied to the transducer.

Transducer housing 11 includes a housing body 31 and a housing cap 32. The transducer used in the illustrated embodiment is in the shape of a so-called TO5 can about 0.3 inch in diameter and 0.3 inch high. Transducer 13 is received in cap 32, which includes a wire passageway for electrical cable 14 to pass through. Housing body 31 is formed with a bore in one end for receiving connecting member 12, which may be secured in place by welding. Housing body 31 is formed to maintain hydraulic communication between the hydraulic fluid and the pressure-sensitive surface 27 of transducer 13. To this end, the inside of housing body 31 is formed to define a second hydraulic cavity, and the pressure-sensitive surface of transducer 13 faces into this cavity for good pressure communication when body 31 and cap 32 are secured together. In the illustrated embodiment the housing body and cap are secured together by a threaded connection. The form of housing may vary and will generally be determined by the particular transducer used in any given embodiment.

Pressure-sensitive transducer 13 is responsive to pressures sufficiently great that it can record the maximum bite force of a strong adult. In practice, this may be achieved with a transducer responding to pressures up to at least about 250 psi. Suitable transducers are commercially available. For example, the illustrated embodiment uses transducer model No. SCC300AHO available from SenSym, Inc. of Milpitas, Calif.

In practice, bite member 10 is covered with sterile sleeve 16 and inserted into the oral cavity. The patient bites down on the bite surface with, for example the upper and lower first molars. The transducer registers a representative electrical signal, which is communicated along cable 14 to other apparatus for analysis. The bite member may then be placed between individual upper and lower teeth or between pairs of teeth, e.g., first and second molars, to map out a strength profile within the oral cavity.

The above descriptions and drawings disclose illustrative embodiments of the invention. Given the benefit of this disclosure, those skilled in the art will appreciate that various modifications, alternate constructions, and equivalents may also be employed to achieve the advantages of the invention. Therefore, the invention is not to be limited to the above description and illustrations, but is defined by the appended claims.

What is claimed is:

1. A probe for making myographic strength measurements in the oral cavity of a patient, comprising:

a bite member sized for insertion into the oral cavity,
said bite member comprising a rigid upper portion, an opposed rigid lower portion and an elastomeric member therebetween, said upper and lower portions being formed and arranged to define a hydraulic cavity with said elastomeric member permitting relative movement therebetween, wherein at least one of said upper and lower portions is formed to provide a bite surface sized for engagement by one or more of the patient's teeth, and said hydraulic cavity includes a hydraulic fluid;

a transducer housing removed from said bite member and arranged to be external to the oral cavity when said bite member is inserted into the oral cavity;

a pressure-sensitive transducer disposed within said transducer housing, said transducer being responsive to a pressure up to at least about 250 psi and providing an electrical signal representative of pressure exerted thereon; and a connecting member connecting said hydraulic cavity with said transducer housing for maintaining said hydraulic cavity in hydraulic communication with said transducer;

whereby a patient biting down on said bite surface imparts a bite force transmitted through relative movement of said rigid upper and lower portions to said hydraulic fluid in said hydraulic cavity which is transmitted to said transducer whereupon said transducer provides said electrical signal indicative of said bite force.

2. The apparatus of claim 1 wherein said bite surface is sized for engagement by at least one and at most two contiguous teeth.

3. The apparatus of claim 2 wherein said bite surface is defined by a centrally disposed, raised portion of said rigid upper portion.

4. The apparatus of claim 1 wherein said connecting member is provided by a rigid tube for communicating hydraulic fluid between said hydraulic cavity and said transducer, said tube also defining a handle for manipulating said bite member in said oral cavity.

* * * * *